United States Patent [19]

Szmuszkovicz

[11] 4,159,339
[45] Jun. 26, 1979

[54] N-(2-AMINOCYCLOHEPTYL) ALKANOYLANILIDES

[75] Inventor: Jacob Szmuszkovicz, Kalamazoo, Mich.

[73] Assignee: The Upjohn Company, Kalamazoo, Mich.

[21] Appl. No.: 910,749

[22] Filed: May 30, 1978

Related U.S. Application Data

[60] Division of Ser. No. 885,515, Mar. 15, 1978, which is a continuation-in-part of Ser. No. 779,593, Mar. 21, 1977, abandoned.

[51] Int. Cl.$^2$ .................. A61K 31/40; A61K 31/445; C07D 207/12
[52] U.S. Cl. ................................ 424/274; 260/326.4; 424/267
[58] Field of Search ............................... 424/267, 274; 260/326.2, 326.4

[56] References Cited

U.S. PATENT DOCUMENTS 3,510,492  5/1970  Szmuszkovicz ................. 260/293.79

*Primary Examiner*—Stanley J. Friedman
*Attorney, Agent, or Firm*—John T. Reynolds

[57] ABSTRACT

N-(2-aminocycloheptyl)N-alkanoylanilides and their 2-N-oxides of the formula

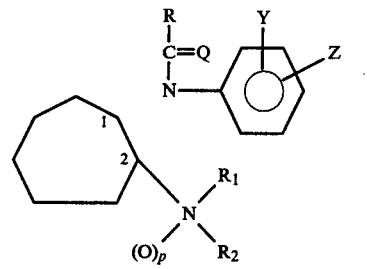

e.g., trans-3,4-dichloro-N-[2-(dimethylamino)cycloheptyl]propionanilide, and their pharmacologically acceptable salts, have been found to possess potent Central Nervous System antidepressant properties. Many of them are new.

These compounds are promising antidepressant drugs which are characterized by lower toxicity than imipramine, and long acting activity which may allow longer durations between administrations, e.g., once a day. Pharmaceutical compositions containing these compounds and a process for treating conditions of depression with these compositions are disclosed.

10 Claims, No Drawings

N-(2-AMINOCYCLOHEPTYL) ALKANOYLANILIDES

CROSS REFERENCE TO RELATED APPLICATIONS

This is a division of U.S. application Ser. No. 885,515, filed Mar. 13, 1978, which is a continuation-in-part application Ser. No. 779,593, filed Mar. 21, 1977, now abandoned.

INTRODUCTION

This invention relates to amino-cycloaliphatic amides which have central nervous system pharmaceutical utility. More particularly this invention provides some new pharmaceutical preparations containing cis and/or trans N-(2-aminocycloheptyl)-N-alkanoylanilide compounds or their pharmacologically acceptable salts which have been found to have potent central nervous system (CNS) antidepressant properties which makes them useful as antidepressant drugs, when formulated into useful pharmaceutically usable composition forms, and administered in appropriate dosages.

BACKGROUND OF THE INVENTION

W. G. Stoll et al., in Helvetica Chemica Acta, Vol. 34, (1951), pp. 1937 to 1943 disclose N-[2-(dimethylamino)cyclohexyl]aniline and procedures for making it from N-(2-hydroxycyclohexyl)aniline and suggest that the compounds therein have antihistamine pharmacological properties, but nothing is said about the compounds of this invention or their use as antidepressant drugs.

J. W. Lewis et al., in an article entitled "The Reactions of Aromatic Nitroso-compounds with Enamines. Part I. The Reaction of Nitrosobenzene with 1-Morpholin-1-cyclohexene" in *J. Chem. Soc.* (London) (1972), Perkins Transactions I, Part III, pp. 2521–2524 discloses *inter alia* N-(2-morpholin-1-ylcyclohexyl)-phenylhydroxylamine and its hydrochloride salt, but it does not disclose or suggest the alkanoylanilides of this invention or their antidepressant properties.

J. W. Lewis et al., in an article entitled "Chemistry and Biological Activity of N-Substituted Hydroxylamines" in *J. Pharmaceutical Sciences*, December, 1974, Vol. 63, No. 12, pp. 1951–1953 discloses some N-arylhydroxylamines such as N-[2-(N-pyrrolidinyl)cyclohexyl]-N-phenylhydroxylamine but these do not have useful CNS properties. Diuretic activity is alleged therein for the alcohols such as [2-(N-piperidinyl)cyclohexyl]-(4-methoxyphenyl)methanol and when the alcohol is acetylated, CNS depressant activity is said to appear. It also discloses the reaction of propionyl chloride with N-[2-(N-piperidinyl)-1,1-dimethylethyl]-N-phenylhydroxylamine to form the N-chloro compound which is then converted to a mixture of chlorinated aniline derivatives. That publication does not teach the compounds disclosed herein, how to make them, nor does it suggest the antidepressant properties which have been found for the compounds disclosed and claimed herein.

Szmuszkovicz U.S. Pat. No. 3,510,492 discloses and claims some 2-anilino- and 2-anilinomethylcycloalkylamines which are useful as antidiabetic drugs in that they can be administered in low dosages for reducing blood sugar. However, that patent in column 2, structure IV generically suggests some of the Formula I compounds of the pharmaceutical preparations and use process of this invention as chemical intermediates enroute to the 2-anilinocycloalkyl amines thereof, but it does not suggest any end product practical utility for those structures IV compounds and it does not disclose the compounds claimed herein.

OBJECTS OF THE INVENTION

It is an object of this invention to provide some new N-(2-aminocycloheptyl)alkanoylanilides which have been found to have promising antidepressant drug properties.

It is a more specific object of this invention to provide new N-(2-aminocycloheptyl)alkanoylanilides which are useful as antidepressant drugs, the preferred compounds having lower toxicity than imipramine and longer lasting activity which allows longer durations between administrations.

It is another object of this invention to provide compositions, useful in pharmaceutical dosage unit form, for treating conditions of depression in mammals including humans comprising an N-(2-aminocycloheptyl)alkanoylanilide as described herein, or a pharmacologically acceptable salt thereof in a pharmaceutical carrier.

It is another object of this invention to provide a process for treating conditions of depression in mammals including humans with these compositions containing an N-(2-aminocycloheptyl)alkanoylanilide, or a pharmacologically acceptable salt thereof.

Other objects, aspects and advantages of this invention will be apparent from reading the specification and claims which follow.

SUMMARY OF THE INVENTION

Briefly, this invention provides pharmaceutical preparations of some cis and trans N-(2-aminocycloheptyl)-N-alkanoylanilides of the formula

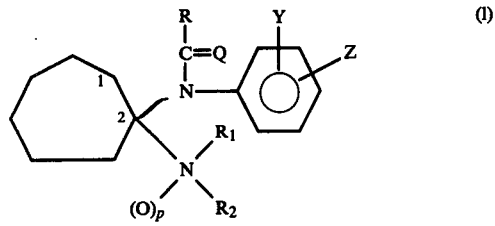

and their pharmacologically acceptable salts, wherein P, Q, R, $R_1$, $R_2$, Y and Z are as defined hereinbelow, which have been found to possess potent central nervous system (CNS) antidepressant properties. A preferred examples for this use is trans-3,4-dichloro-N-[2-(dimethylamino)cycloheptyl]propionanilide. This invention also includes these compounds (I) which are new, per se, and their acid addition salts, especially their pharmacologically acceptable salts. These compounds are useful, in appropriate pharmaceutical dosage unit form, for administration to humans in dosages of from 4–400 mg. per day as part of the therapy in treating conditions of depression. In standard laboratory animals used to determine these properties, these compounds suggest fast onset of the antidepressant characteristics of the drug, the preferred compounds having, in addition, lower toxicity than a standard antidepressant drug, imipramine, in standard laboratory tests, and longer duration of activity of the test compound in the test animal. These characteristics of these compounds will make them useful for the administration of these compounds as antidepressant drugs in smaller amount and/or for longer durations between administration, e.g., once a day, for a given desired antidepressant response.

This invention also includes a process for treating depression with these compositions containing these above formula I compounds, or pharmaceutically acceptable salts thereof, and a pharmaceutical carrier, which compositions are useful in dosage unit form for treating conditions of depression in mammals including humans.

DETAILED DESCRIPTION OF THE INVENTION

More specifically, one aspect of this invention provides new pharmaceutical preparations containing compounds of the formula

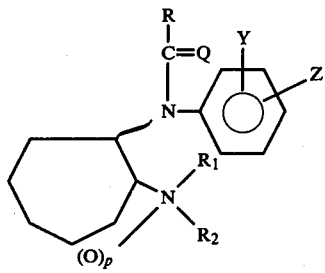

wherein the wavy line (∼) on the 1-position of the cycloheptyl ring denotes cis- or trans-configuration relative to the amino group in the 2-position of the cycloheptyl ring;

p is zero or 1;

Q is oxygen or sulfur;

R is $C_1$ to $C_3$-alkyl, $C_3$ to $C_6$-cycloalkyl, vinyl (—CH=$CH_2$), ethoxy or methoxymethyl;

$R_1$, taken separately, is $C_1$ to $C_3$-alkyl;

$R_2$, taken separately, is $C_1$ to $C_3$-alkyl, and when $R_1$ is $C_1$ to $C_3$-alkyl, $R_2$ can be —$CH_2CH_2N(CH_3)_2$,
—$CH_2CH_2CH_2N(CH_3)_2$,
—$CH_2C_6H_5$(benzyl),
—$CH_2CH_2$-$C_6H_5$ (2-phenylethyl), or
—$C_3$-$C_6$-(allylic)alkenyl and when $R_1$ and $R_2$ are taken together with the nitrogen to which they are bonded, they complete an N-pyrrolidinyl or an N-piperidinyl ring;

each of Y and Z is selected from the group consisting of hydrogen, a halogen having an atomic number of from 9 to 35, trifluoromethyl, $C_1$ to $C_2$-alkyl, azido(-$N_3$), and $C_1$ to $C_2$-alkyloxy, and when Y is trifluoromethyl or azido, Z is hydrogen; when Y is $C_1$ to $C_2$-alkyloxy and Z is hydrogen, the $C_1$ to $C_2$-alkyloxy is in the 3-position; when Y and Z are both halogens or $C_1$ to $C_2$-alkyloxy, they are present in 3- and 4- or 3- and 5-positions, and the acid addition salts thereof, preferably the pharmacologically acceptable acid addition salts thereof. On occasion, the compounds or their acid addition salts in their crystalline state are isolated as solvates, i.e., with a discrete quantity of solvent, e.g., water, ethanol, and the like, associated physically, and thus the solvent is removable without effective alteration of the chemical entity per se and are included with the compounds per se herein.

In the above formula I compounds, the term "$C_1$ to $C_3$-alkyl" means methyl, ethyl, n-propyl and isopropyl; the term "$C_3$ to $C_6$-cycloalkyl" means cyclopropyl, cyclobutyl, cyclopentyl and cyclohexyl groups; the term "$C_3$ to $C_6$-(allylic)alkenyl" includes the non-adjacent double bond groups, e.g., allyl, 2-butenyl and 2-methyl-2-butenyl, 2-pentenyl and 3-methyl-2-pentenyl, and the various 2-hexenyl groups; and the halogens having atomic numbers of from 9 to 35 are fluorine, chlorine and bromine.

The preferred compounds of this invention are those of the trans configuration.

A preferred subgroup of the above compounds and the pharmaceutical preparation forms thereof are those wherein R is $C_1$ to $C_3$-alkyl, preferably ethyl; $R_1$ and $R_2$ are each $C_1$ to $C_3$ alkyl; and at least one of Y and Z are halogen having an atomic number of from 9 to 35, preferably in the 3- and 4-positions, $C_1$ to $C_2$-alkyloxy or trifluoromethyl in the 3-position, or methyl in the 3- or 4-position in combination with one of the above halogens at the adjacent 3- or 4-position, and the pharmacologically acceptable salts thereof. Examples of such compounds include the following:

3,4-dichloro-N-[2-(dimethylamino)cycloheptyl]propionanilide;

3-trifluoromethyl-N-[2-(dimethylamino)cycloheptyl]-propionanilide, 3,4-dichloro-N-[2-(diethylamino)cycloheptyl]propionanilide, 3-chloro-4-methyl-N-[2-(dimethylamino)cycloheptyl]-propionanilide, 4-chloro-3-methyl-N-[2-(diethylamino)cycloheptyl]-propionanilide, 3chloro-N-[2-(dimethylamino)cycloheptyl]propionanilide, 4-chloro-N-[2-(dimethylamino)cycloheptyl]propionanilide, 3-methoxy-4-chloro-N-[2-(dimethylamino)cycloheptyl]-propionanilide, 3-methoxy-N-[2-(dimethylamino)cycloheptyl]propionanilide, 3-bromo-N-[2-(dimethylamino)cycloheptyl]propionanilide, and 3-fluoro-N-[2-(dimethylamino)cycloheptyl]propionanilide, especially these compounds in the trans configurations, and the pharmacologically acceptable salts thereof.

Another preferred sub-group of the above compounds are those wherein R is $C_1$ to $C_3$-alkyl, preferably ethyl, $R_1$ and $R_2$ are taken together with the nitrogen to which they are bonded to complete an N-pyrrolidinyl or N-piperidinyl ring, and at least one of Y and Z is a halogen having an atomic number of from 9 to 35 in the 3- and/or 4-positions. Examples of such compounds include:

3-fluoro-N-[2-(N-pyrrolidinyl)cycloheptyl]propionanilide, 3,4-dichloro-N-[2-(N-piperidinyl)cycloheptyl]propionanilide;

3-bromo-N-[2-(N-pyrrolidinyl)cycloheptyl]propionanilide, 4-chloro-N-[2-(N-pyrrolidinyl)cycloheptyl]propionanilide, 3,4-dichloro-N-[2-(N-pyrrolidinyl)cycloheptyl]propionanilide, 3,4-difluoro-N-[2-(N-pyrrolidinyl)cycloheptyl]propionanilide, and 3,4-dibromo-N-[2-(N-pyrrolidinyl)cycloheptyl]propionanilide, especially these compounds in their trans configuration and the pharmacologically acceptable salts thereof.

Another preferred sub-group of the above compounds are those wherein R is $C_3$ to $C_6$-cycloalkyl, $R_1$ and $R_2$ are $C_1$ to $C_3$-alkyl, and at least one of Y and Z are halogen having an atomic number of from 9 to 35 in the 3- or 4-position, trifluoromethyl in the 3-position, or methyl in the 3- or 4-position in combination with one of the above halogens in the adjacent 3- or 4-positions, and the pharmacologically acceptable salts thereof. Examples of such compounds include:

3,4-dichloro-N-[2-dimethylaminocycloheptyl]cyclobutanecarboxanilide, 3,4-dichloro-N-[2-dimethylaminocycloheptyl]cyclohexanecarboxanilide, 3-bromo-4-methyl-N-[2-dimethylaminocycloheptyl]cyclobutanecarboxanilide, 3,4-dichloro-N-[2-dimethylaminocycloheptyl]cyclopropanecarboxanilide, 3-trifluoromethyl-N-[2-diethylaminocycloheptyl]cyclopropanecarboxanilide, 3,4-dibromo-N-[2-diethylaminocycloheptyl]cyclopropanecarboxanilide, 3-chloro-4-methyl-N-[2-dimethylaminocycloheptyl]cyclopropanecarboxanilide, 3-bromo-4-methyl-N-[2-dimethylaminocycloheptyl]cyclohexanecarboxanilide, 3-trifluoromethyl-N-[2-dimethylaminocycloheptyl]cyclohexanecarboxanilide, and the pharmacologically acceptable salts thereof.

Examples of acid addition salts, including pharmacologically acceptable salts of the above formula I compounds include those of hydrochloric, methanesulfonic, pamoic, hydrobromic, sulfuric, acetic, cyclohexanesulfamic, p-toluenesulfonic, succinic, β-naphthalenesulfonic, maleic, fumaric, citric, lactic and oxalic acids.

To use these new compounds in pharmaceutical antidepressant drug product form they are compounded or formulated into usual pharmaceutical compositions, e.g., oral dosage forms such as tablets, powders, capsules and solutions or suspensions in a suitable solvent or suspending vehicle, and parenteral dosage forms such as dry powder in a sterile sealed container to be mixed with a sterile solvent just prior to administration, sterile solutions or suspensions in water or other suitable solvents or suspending agents, to provide a convenient means for administering to the patient in an amount effective to alleviate the conditions of depression, in association with a pharmaceutical carrier. Generally, daily doses ranging from about 4 mg. to about 400 mg., preferably 50 to 200 mg., of the formula I compound or its pharmacologically acceptable salt, depending upon the potency of the formula I compound, the condition being treated, the weight of the patient and other factors of concern to the patient's physician would be given to such patients.

The formula I compounds where Q is oxygen (=O) and p is zero can be prepared by (a) heating a mixture of a compound of the formula

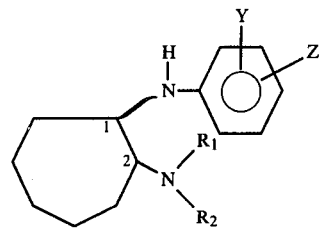

wherein $R_1$, $R_2$, Y and Z are as defined above, and an anhydride of the appropriate organic carboxylic acid of the formula R—COOH on a steam bath, or at an equivalent temperature, for a time sufficient to form the N-acylated product of formula I where R is as defined above, Q is oxygen and p is zero, (b) adding an aqueous medium to the step (a) reaction mixture in an amount sufficient to decompose excess anhydride therein, (c) adding an alkali metal hydroxide or its equivalent to the step (b) reaction mixture in an amount sufficient to neutralize excess acid present therein and to make the mixture pH basic, (d) extracting the N-acylated product (I) into a water immiscible organic liquid solvent, e.g., ether solvents such as diethyl ether, tetrahydrofuran (THF) or dioxane, or chloroform, carbon tetrachloride, methylene chloride, ethylene dichloride, or the like (e) separating the organic liquid phase containing the N-acylated product (I) from the aqueous phase, and (f) recovering the corresponding N-acylated compound (I) from the organic liquid phase, usually after washing the organic liquid phase one or more times with aqueous media such as sodium chloride solution, sodium bicarbonate solution or water to extract components soluble in those aqueous media, separating the aqueous phases, drying the washed organic phase with drying agents such as magnesium sulfate or sodium or calcium sulfate, and then evaporating off the organic solvent. Further purification can be done by forming an acid salt of the N-acylated amide product (I) and then recrystallizing the amide salt from an appropriate solvent or mixture of solvents.

These formula I compounds, immediately above, can also be prepared by (a) adding a solution of the appropriate carboxylic acid halide R—C(O)—X where R is as defined above and X is chloride or bromide to a cooled ($-5°$ to $+10°$ C.) mixture of the diamine (II), and a tertiary amine which will form a tertiary amine chloride or bromide salt in the mixture, e.g., a $C_1$ to $C_4$-trialkylamine, e.g., trimethylamine, triethylamine, tributylamine, or pyridine, lutidine, N,N-dimethylaniline or the like, in an organic liquid solvent for the mixture such as an ether solvent such as diethyl ether, THF, dioxane or the like, while agitating the mixture until the corresponding N-acylated compound (I) is formed, (b) adding an aqueous alkali metal bicarbonate solution to the reaction mixture of step (a), (c) separating the aqueous from the organic liquid phases, (d) washing the organic liquid phases with aqueous wash liquids as described above, (e) drying the organic phase, and (f) recovering the N-acylated compound (I) from the resulting organic liquid mixture. The N-acylated amide compound (I) can be further purified by formation of an acid addition salt thereof, e.g., the hydrochloric acid, or maleic acid addition salt thereof, and recrystallization of the amide salt from an appropriate solvent or solvent mixture.

The formula I compounds which do not contain a reactive aliphatic carbon-to-carbon double bond in the molecule, and wherein Q is oxygen (=U) and p is zero, can be converted to their N-oxides by reaction of such formula I aminoamide or its salt with a percaboxylic acid by known procedures to obtain the corresponding formula I compound where p is 1.

The corresponding N-thioacyl amino anilide compounds can be prepared by heating to reflux the corresponding N-acyl(C=O) amino anilide (formula I compound) with a thiolating agent such as phosphorus pentasulfide or diethyldithiophosphate [P(S)SH(OC$_2$H$_5$)$_2$] in an appropriate solvent such as pyridine for a time sufficient to effect replacement of the acyl oxygen atom with sulfur, and then recovering and purifying the N-thioacyl aminoanilide compound by known procedures. If the N-oxides of the Q is S compounds are to be made, the N-oxide is prepared first and the resulting N-oxide is thiolated as described above to form the formula I compound where Q is =S and p is 1.

Further exemplification of these process procedures appear in the detailed examples.

The trans-diamine starting materials (II) of the formula

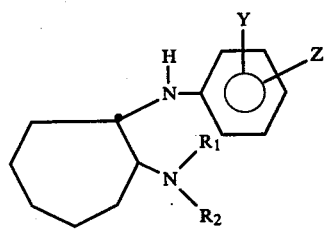

wherein R$_1$, R$_2$, Y and Z are as defined above can be prepared by reacting 1,2-cycloheptene oxide (IIIa)

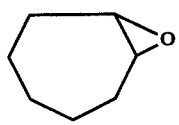

with the selected HNR$_1$R$_2$ amine in water to form the trans-2-aminocyclopentanol of the formula IIIb

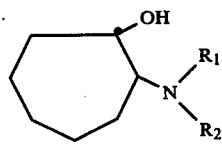

which amino-alcohol (IIIb) is treated with sodium hydride and then with methanesulfonyl chloride to form unrecovered mesylate of the formula IV

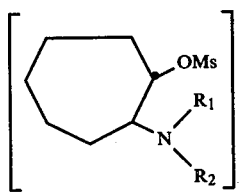

wherein Ms denotes CH$_3$SO$_2$-group and that reaction mixture is treated with the selected substituted aniline of formula V

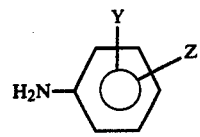

to form the diamine (II). Examples of this procedure are given hereinbelow in the detailed descriptions.

Examples of the carboxylic acid anhydrides which can be used to prepare the compounds of this invention include acetic anhydride, propionic anhydride, isobutanoic acid anhydride, n-butanoic acid anhydride, cyclopropanecarboxylic acid anhydride, acrylic acid anhydride, and the like. The preferred anhydride is propionic acid anhydride. The carboxylic acid halides are exemplified by acetyl chloride or bromide, propionyl chloride or bromide, acryloyl chloride or bromide, cyclohexanecarbonyl chloride or bromide, n- and isobutanoylchloride, or bromide, cyclopropanecarbonyl chloride or bromide, ethyl formate, methoxyacetyl chloride or bromide, and the like. We have found that, in general, the most potent antidepressant compounds are made from those compounds having an N-propionyl moiety, so that in the formula I compound R is preferably ethyl.

When it is desired that the formula II have an allyl group in the R$_2$ position, an alternate method can also be used: the amino-amide is prepared as described above using an alkyl benzylamine to form the amino-alcohol (IIIb), and that amino-alcohol is carried through the intermediate (IV), and (V) reactions to form the diamine. The resulting diamine is then hydrogenated catalytically, preferably in the presence of palladium on carbon catalyst, to remove the benzyl group in the R$_2$ position and from the trans diamine of the formula VI.

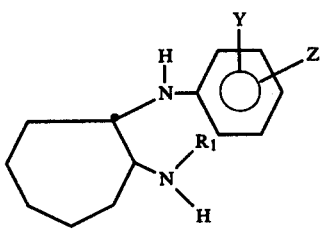

The trans-diamine (VI) is then reacted with a C$_3$–C$_6$(allylic)alkenyl chloride or bromide to form the compound of formula VII

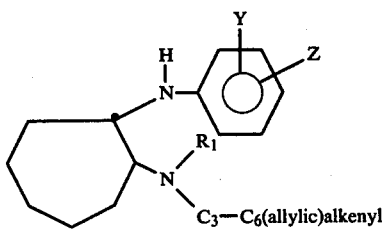

which diamine (VII) is used as an intermediate in a reaction with the selected carboxylic acid anhydride or acid chloride or bromide, to form the N-acylated product of the formula

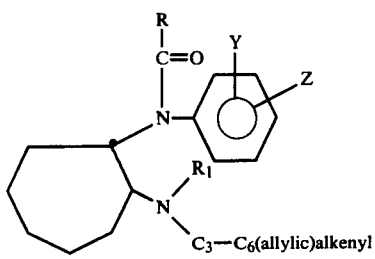

(VIII)

in which formulae Ia, IIIb, IV, V, VI, VII and VIII, R, R₁, Y and Z are as defined above.

Preparation of cis amino amide compound of invention:

The method of J. W. Lewis et al., *J. Pharm. Sci.*, 63, 1951 (1974) using 1-dialkylaminocyclopentene (enamine) and nitrosoaryl as starting materials can be applied to the corresponding cycloheptane enamines to obtain cis-1,2-diaminocycloheptane which is subsequently reacted with carboxylic acid anhydride or carboxylic acid halide as described above to give the product amino-amide.

A preferred method, which is that used for this invention, involves reaction of cycloheptene oxide with an aniline in the presence of strong acid to give the compound of formula

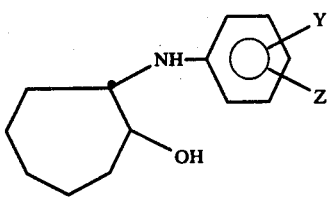

(IX)

which is subsequently reacted with carboxylic acid anhydride followed by reaction with base to isolate the compound of formula

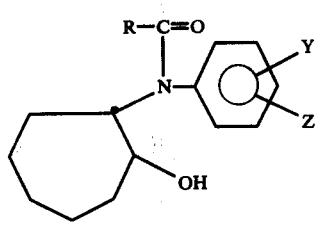

(X)

Oxidation of the alcohol leads to the compound of formula XI

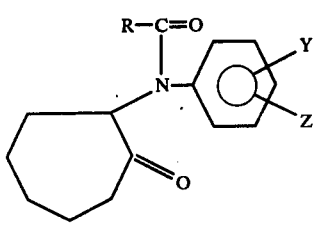

(XI)

which when reacted with primary or secondary amine and a reducing agent such as sodium cyanoborohydride, and the like, gives a compound of the formula

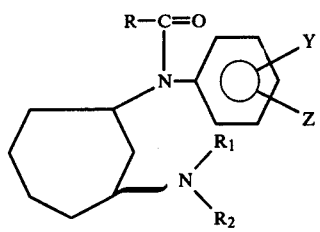

(XII)

wherein R₂ is not C₃–C₆(allylic)alkenyl. The cis-/trans mixture of compounds which results can be separated physically by column chromatography on silica gel to isolate the cis-isomer of the formula

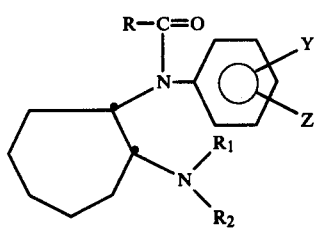

(XIII)

wherein R, R₁, R₂, Y and Z are as defined above. For the preparation of cis amino-amides wherein R₂ is C₃-C₆-(allylic)alkenyl, the above sequence of steps is followed using a primary amine together with the reducing agent referred to above. After isolation of the cis amino amide, its reaction with a C₃–C₆(allylic)alkenyl halide yields the cis amino-amide wherein R₂ is C₃–C₆-(allylic)alkenyl.

The thio analogs of such cis amino-amides can be prepared as described earlier in this specification.

Examples of additional useful compounds of formula I of this invention include the following compounds, preferably in their trans-configuration N-[2-(dimethylamino)cycloheptyl]propionanilide, 3-methyl-N-[2-(dimethylamino)cycloheptyl]propionanilide, 3-methoxy-N-[2-(dimethylamino)cycloheptyl]propionanilide, 3,4-dichloro-N-{2-[N-methyl-N-(2-dimethylaminoethyl)amino]cycloheptyl}propionanilide, 3,4-dichloro-N-{2-[N-methyl-N-(3-dimethylaminopropyl)amino]cycloheptyl}propionanilide, N-[2-(dimethylamino)cycloheptyl]acetanilide, N-[2-(dimethylamino)cycloheptyl]butyranilide, 3-trifluoromethyl-N-[2-(N-methyl-N-benzylamino)-cycloheptyl]propionanilide, 3,4-dibromo-N-{2-[N-ethyl-N-(2-phenylethyl)amino]-cycloheptyl}propionanilide, 3-chloro-4-methyl-N-[2-(N-methyl-N-allylamino)cycloheptyl]propionanilide, 4-bromo-3-methyl-N-[2-(N-pyrrolidinyl)cycloheptyl]-propionanilide, 3,4-difluoro-N-{2-[N-methyl-N-(2-dimethylaminoethyl)-amino]cycloheptyl}propionaniline, 3-chloro-4-fluoro-N-[2-(dimethylamino)cycloheptyl]-propionanilide, 3,4-dibromo-N-[2-(dimethylamino)cycloheptyl]propionanilide, 3,4-dimethyl-N-[2-(dimethylamino)cycloheptyl]propionanilide, 3,4-dichloro-N-[2-(dimethylamino)cycloheptyl]-butyranilide, 3,4-dichloro-N-[2-(dimethylamino)cycloheptyl]-N-cyclopropanecarboxanilide,
3,4-dichloro-N-[2-(dimethylamino)cycloheptyl]thiopropionanilide,
3,4-dichloro-N-[2-(dimethylamino)cycloheptyl]-N-acrylanilide,
3,4-dichloro-N-[2-(dimethylamino)cycloheptyl]isobutyranilide,
3-bromo-N-[2-(N-methyl-N-benzylamino9cycloheptyl]-butyranilide,
3-chloro-4-fluoro-N-[2-(N-pyrrolidinyl)cycloheptyl]-cyclopropanecarboxanilide,
3,5-dibromo-N-[2-(N-methyl-N-2-phenylethylamino)-cycloheptyl]propionanilide,
3,4-dichloro-N-[2-dimethylaminocycloheptyl]methoxyacetanilide,
3,4-dichloro-N-[2-dimethylaminocycloheptyl]carbethoxyanilide,
3-methyl-4-chloro-N-[2-diethylaminocycloheptyl]-propionanilide,
3-trifluoromethyl-N-{2-[N-methyl-N-2-butenyl-]aminocycloheptyl}cyclohexanecarboxanilide,
3-ethoxy-4-bromo-N-[2-dimethylaminocycloheptyl]-propionanilide,
4-azido-N-[2-(dimethylamino)cycloheptyl]propionanilide.

and the like, the 2-N-oxides of the above compounds which do not contain aliphatic unsaturation, and their acid addition salts.

If desired, the formula I compounds of this invention can be resolved into their respective d- and l-optical isomers by methods known in the art. In this case the optical resolution can be done by at least two different routes. The resolving agents by either route are any of the known resolving agents such as optically active camphorsulfonic acid, bis-p-toluoyltartaric acid, tartaric acid, and diacetyl tartaric acid which are commercially available and which are commonly used for resolution of amines (bases) as for example in *Organic Syntheses*, Coll. Vol. V., p. 932 (1973), resolution of R-(+) and S-(−)-α-phenylethyl amine with (+)-tartaric acid.

By the first method for resolving the compounds of this invention, for example, one of the amino amide compounds can be converted into its optically active diastereomeric salts by reaction with an optically active acid, examples of which are mentioned above, in a manner standard in the isomer resolution art. These diastereomeric salts can then be separated by conventional means such as differential crystallization. Diastereomeric salts have different crystallization properties, which are taken advantage of in this separation. On neutralization of each diastereomeric salt with aqueous base, the corresponding optically active form of the free aminoamide can be obtained, each of which can subsequently and separately be converted as previously described in the examples to the desired acid addition salt.

By the second method, which in the case of some of these compounds is preferred, the formula I compounds can be made into their respective d- and l-isomers, by first resolving cis- or trans-1,2-cycloaliphatic unsymmetrically substituted diamine into its respective d- and l-isomers by treatment with the resolving agent, crystallization, separation, and regeneration of the respective trans-d-diamine, trans-l-diamine, or the cis-d-diamine and cis-l-diamine, and then reacting the respective resolved diamine starting material with the desired carboxylic acid anhydride or halide to form the respective cis- or trans-d- or l-compound of formula I, which can then be converted to any desired pharmaceutically acceptable acid addition salt by procedures exemplified above.

If the acid addition salt used to extract the formula I compound from its reaction mixture is not itself pharmacologically acceptable, the free aminoamide base (I) can be prepared from the acid salt, and thereafter converted to a pharmacologically acceptable salt, by known procedures.

In the use of these compounds of formula I as antidepressant drugs the selected compound of formula I is to be the antidepressant active ingredient is mixed with suitable pharmaceutical diluents to obtain pharmaceutical compositions suited for oral, parenteral and rectal use in dosage unit form, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, corn starch, stearic acid, methylcellulose and the like may be used as carriers or for coating purposes. Water and oils, e.g., coconut oil, sesame oil, safflower oil, cottonseed oil, peanut oil may be used for preparing solutions or suspensions of the active drug. Sweetening, coloring and flavoring agents may be added. The specifications for the dosage unit forms of these formula I compounds will vary somewhat from compound to compound and dependent upon the physical characteristics of the formula I compound or its pharmacologically acceptable salt, the particular patient's weight and age, and the particular effect sought to be achieved. The pharmaceutical dosage unit forms of these compounds are prepared in accordance with the preceding general description to provide from about 4 to about 400 mg. of the formula I compound or its pharmacologically acceptable salt per dosage unit form. The amount of the formula I compound prescribed in pharmaceutical dosage unit form is that amount sufficient to obtain in the patient a relief from the condition of depression effect at a non-toxic dosage level.

The following detailed procedures and examples further describe and illustrate how to make and use the starting amines and the compounds of this invention. All temperatures are in degrees Centigrade unless otherwise indicated. For brevity, the term THF means tetrahydrofuran, NMR means nuclear magnetic resonance spectrum, IR means infrared spectrum, UV means ultraviolet spectrum, ether means diethyl ether, NaOH means sodium hydroxide, MgSO₄ means anhydrous magnesium sulfate, and MeOH means methanol.

EXAMPLE 1

Preparation of trans-3,4-dichloro-N-[2-(dimethylamino)cycloheptyl]-propionanilide and its maleate salt A. Preparation of trans-2-dimethylaminocycloheptanol, and its fumarate salt A mixture of 89.0 g. (0.80 mole) of cycloheptene oxide and 40% aqueous dimethylamine (275 ml., 2.4 mole) is shaken in a rocking pressure bomb at about 125° for 24 hours. A brown solution is obtained. The reaction mixture solution is then saturated with about 50 g. of potassium carbonate, and two layers are formed. One milliliter of 40% aqueous potassium hydroxide is added, the resulting mixture is extracted three times with ether, the ether layers are combined and dried with anhydrous magnesium sulfate and then concentrated by evaporation of ether. Distillation of the residue gives 114.6 g. (91% yield) of the titled amino alcohol, b.p. 98°–100°/10 mm. NMR, IR and mass spectrum analyses are in accord with the assigned structure.

The crystalline fumarate salt of the titled amino alcohol is prepared and recrystallized from methanol/ether, m.p. 136°–137° C.

Anal. Calcd. for $C_9H_{19}NO$ (Amino Alcohol): Calcd.: C, 68.74; H, 12.18; N, 8.91; Found: C, 68.48; H, 12.39; N, 8.53.

B. Preparation of trans-N-[2-(dimethylamino)cycloheptyl]-3,4-dichloroaniline, and its oxalic acid salt A mixture of 2-dimethylaminocycloheptane-1-ol (15.7 g., 0.10 mole) and 4.8 g. (0.10 mole) of sodium hydride (50% dispersion) in 50 ml. of THF is heated on a steam bath for one hour and then cooled in ice. Methanesulfonyl chloride (11.5 g., 0.10 mole) in 25 ml. of THF is added over 30 minutes. Subsequently, 3,4-dichloroaniline (32.4 g., 0.20 mole) is added in one portion. The THF solvent is removed by distillation and heating of the mixture on a steam bath is continued overnight. Addition of 200 ml. of 20% aqueous sodium hydroxide is followed by heating for one hour. The reaction mixture is extracted with 10% aqueous hydrochloric acid. The aqueous acid layer is washed with ether, basified with 40% aqueous sodium hydroxide and extracted with 250 ml. of ether. The ether layer is washed with saturated aqueous sodium chloride solution, dried with magnesium sulfate and the ether is removed by evaporation. The residual oil is distilled to give 17.3 g. (57% yield) of the titled amine (b.p. 170°–180°/0.3 mm).

The oxalic acid salt of the titled amine is prepared from 5.2 g. (0.057 mole) of oxalic acid and the diamine prepared above in a solvent mixture which consists of 25 ml. of methanol and 200 ml. of ether. Recrystallization from the same solvent mixture gives 15.5 g. (69% yield) of the oxalic acid salt of the titled diamine, m.p. 153°–154° C. The NMR, IR, UV and mass spectra are in accord with the assigned structure.

Anal. Calcd. for $C_{15}H_{22}N_2Cl_2.C_2H_2O_4$: Calcd.: C, 52.15; H, 6.18; N, 7.16; Cl, 18.12; Found: C, 52.25; H, 6.34; N, 6.98; Cl, 18.23.

C. Preparation of trans-3,4-dichloro-N-[2-(dimethyl-amino)cycloheptyl]-propionanilide and maleate salt To an ice-cooled solution of trans-N-[2-(dimethyl-amino)cycloheptyl]-3,4-dichloroaniline (3.01 g., 0.01 mole) and 2.02 g. (0.02 mole) of triethylamine in 100 ml. of ether there is added 1.85 g. (0.02 mole) of propionyl chloride over 30 minutes. The reaction mixture is stirred at room temperature overnight. Then 100 ml. of saturated sodium bicarbonate aqueous solution is added. The organic layer is washed with water followed by saturated sodium chloride solution and then dried over anhydrous magnesium sulfate and concentrated to a yellow oil residue of the titled propionanilide. This oil is dissolved in a mixture of methanol (10 ml.) and ether (75 ml.) and maleic acid (1.16 g., 0.01 mole) is added. A crystalline precipitate results which is recrystallized from the same solvent mixture to give 3.90 g. of the titled amino-anilide maleate salt (82% yield, m.p. 165°–166° C.). NMR, IR, UV and mass spectra are in accord with the structure.

Anal. Calcd. for $C_{18}H_{26}N_2Cl_2O.C_4H_4O_4$: Calcd.: C, 55.81; H, 6.39; N, 5.92; Cl, 14.98, Found: C, 56.05; H, 6.46; N, 6.07; Cl, 15.16.

EXAMPLE 2

Preparation of trans 3-trifluoromethyl-N-[2-(1-pyrrolidinyl)cycloheptyl]-propionanilide Following the procedure of Example 1 but initially substituting in Part A a stoichiometric equivalent amount of pyrrolidine for the dimethylamine to obtain trans-2-(N-pyrrolidinyl)cycloheptanol and subsequently substituting in Part B a stoichiometric equivalent amount of 3-trifluoromethylaniline for the 3,4-dichloroaniline, there is obtained trans-N-[2-(N-pyrrolidinyl)cycloheptyl]-3-trifluoromethylaniline, which can be converted to its propionanilide and, if desired, to its acid addition salt such as the hydrochloride or maleate by the procedure of Example 1, Part C.

EXAMPLE 3

Preparation of trans-3,4-dichloro-N-[2-(dimethylamino)cycloheptyl]-propionanilide-2-N-oxide.

A stoichiometrically equivalent quantity of 85% m-chloroperbenzoic acid in chloroform is added dropwise to an equimolar amount of trans-3,4-dichloro-N-[2-(dimethylamino)cycloheptyl]propionanilide, prepared as described in Example 1, with ice cooling; the mixture is stirred overnight at room temperature and is then evaporated to dryness. After several washings and concentrations, the titled 2-N-oxide compound is obtained.

EXAMPLE 4

Preparation of trans-4-bromo-N-[2-(dimethyl-amino)cycloheptyl]thio-propionanilide Molar equivalent quantities of trans-4-bromo-N-[2-(dimethylamino)cycloheptyl]propionanilide, prepared analogously to the procedure described in Example 1, and phosphorous pentasulfide are dissolved in pyridine and the mixture is heated at the reflux temperature; the pyridine is removed by distillation and the title compound is isolated after weak basic and neutral workup procedures. A maleic acid addition salt of such titled thio propionanilide is prepared according to the procedure of Example 1, Part C. Other acid addition salts can be similarly prepared.

EXAMPLE 5

Preparation of 3,4-dichloro-N-[2-(dimethylamino]cycloheptyl]thio-propionanilide

The titled compound is prepared according to the procedure of Example 4 but substituting a stoichiometrically equivalent quantity of 3,4-dichloro-N-[2-(dimethylamino)cycloheptyl]propionanilide for 4-bromo-N-[2-(dimethylamino)cycloheptyl]propionanilide.

EXAMPLE 6

Preparation of cis-3,4-dichloro-N-[2-(dimethylamino)cycloheptyl]propionanilide

A. Preparation of trans-3,4-dichloro-N-[2-hydroxycycloheptyl]aniline

Following the procedure of Example 1, Part A, but substituting the appropriate quantity of 3,4-dichloroaniline for dimethylamine, the product trans-3,4-dichloro-N-[2-hydroxycycloheptyl]aniline is obtained.

B. Preparation of trans-3,4-dichloro-N-(2-hydroxycycloheptyl)propionanilide Following the procedure of Example 1, Parts B and C, but substituting the stoichiometrically equivalent quantities of trans-3,4-dichloro-N-[2-(hydroxy)cycloheptyl]aniline for trans-N-[2-(dimethylamino)cycloheptyl]-3,4-dichloroaniline in Part B and propionic anhydride for propionyl chloride in Part C and heating overnight, there is obtained trans-3,4-dichloro-N-[2-propionoxycycloheptyl]propionanilide; this, on subsequent treatment with one equivalent of potassium hydroxide in ethanol at room temperature, gives trans-3,4-dichloro-N-(2-hydroxycycloheptyl)propionanilide.

C. Preparation of 3,4-dichloro-N-[2-oxocycloheptyl]propionanilide

Treatment of the hydroxyanilide from Part B above with Jones reagent (oxidizing) at room temperature followed by pH neutral work-up procedures gives 3,4-dichloro-N-[2-oxocycloheptyl]propionanilide.

D. Reductive amination of the 2-oxo compound from Part C above

The 3,4-dichloro-N-[2-oxocycloheptyl]propionanilide from Part C above is treated with sodium cyanoborohydride and dimethylamine-dimethylamine hydrochloride in methanol in the presence of 3A molecular sieves; the resulting mixture is worked up under basic pH conditions and the organic residue is chromatographed (column) on silica gel to isolate the cis isomer of 3,4-dichloro-N-[2-(dimethylamino)cycloheptyl]propionanilide.

Following the procedure of Example 1 but substituting for the 3,4-dichloroaniline in Part B thereof a stoichiometrically equivalent amount of one of the following substituted anilines:
(a) 3-fluoroaniline,
(b) 4-bromoaniline,
(c) 3-bromoaniline,
(d) 3,5-dichloroaniline,
(e) 3,4-dibromoaniline,
(f) 3-trifluoromethylaniline,
(g) 3,4-dimethylaniline, or
(h) 3-methoxyaniline there are obtained, respectively,
(a) N-(2-dimethylaminocycloheptyl)-3-fluoroaniline,
(b) N-(2-dimethylaminocycloheptyl)-4-bromoaniline,
(c) N-(2-dimethylaminocycloheptyl)-3-bromoaniline,
(d) N-(2-dimethylaminocycloheptyl)-3,5-dichloroaniline,
(e) N-(2-dimethylaminocycloheptyl)-3,4-dibromoaniline,
(f) N-(2-dimethylaminocycloheptyl)-3-trifluoromethylaniline,
(g) N-(2-dimethylaminocycloheptyl)-3,4-dimethylaniline, or
(h) N-(2-dimethylaminocycloheptyl)-3-methoxyaniline.

Subsequent reaction of each of these N-(2-dimethylaminocycloheptyl)-substituted anilines with propionyl chloride as in Example 1, Part C, there are obtained respectively:
(a) 3-fluoro-N-(2-dimethylaminocycloheptyl)propionanilide,
(b) 4-bromo-N-(2-dimethylaminocycloheptyl)propionanilide,
(c) 3-bromo-N-(2-dimethylaminocycloheptyl)propionanilide,
(d) 3,5-dichloro-N-(2-dimethylaminocycloheptyl)propionanilide,
(e) 3,4-dibromo-N-(2-dimethylaminocycloheptyl)-propionanilide,
(f) 3-trifluoromethyl-N-(2-dimethylaminocycloheptyl)propionanilide,
(g) 3,4-dimethyl-N-(2-dimethylaminocycloheptyl)-propionanilide, and
(h) 3-methoxy-N-(2-dimethylaminocycloheptyl)propionanilide.

Following the procedure of Example 1, Part A, but initially substituting stoichiometrically equivalent amounts of pyrrolidine, diethylamine or N-methyl-N',N'-dimethylaminoethylamine hydrochloride for the dimethylamine, there are obtained, respectively:
N-[2-(N-pyrrolidinyl)]cycloheptanediamine,
N-[2-(diethylamino)]cycloheptanediamine, and
N-[2-(N-methyl-N',N'-dimethylaminoethyl)]cycloheptanediamine.

Each of these cycloheptanediamines, when reacted as in Example 1, Part B, with 3,4-dichloroaniline and subsequently as in Example 1, Part C, with propionyl chloride gives:
3,4-dichloro-N-[2-(N-pyrrolidinyl)cycloheptyl]propionanilide,
3,4-dichloro-N-[2-(diethylaminocycloheptyl)]propionanilide, and
3,4-dichloro-N-[2-(N-methyl-N',N'-dimethylaminoethyl)cycloheptyl]propionanilide, respectively.

Following the procedure of Example 1, Part C, but substituting for the propionyl chloride thereof stoichiometrically equivalent quantities:
(a) cyclopropanecarbonyl chloride,
(b) cyclobutanecarbonyl chloride,
(c) cyclopentanecarbonyl chloride,
(d) cyclohexanecarbonyl chloride, or
(e) methoxyacetyl chloride, there are obtained, respectively:
(a) 3,4-dichloro-N-(2-dimethylaminocycloheptyl)-cyclopropanecarboxanilide,
(b) 3,4-dichloro-N-(2-dimethylaminocycloheptyl)-cyclobutanecarboxanilide,
(c) 3,4-dichloro-N-(2-dimethylaminocycloheptyl)-cyclopentanecarboxanilide,
(d) 3,4-dichloro-N-(2-dimethylaminocycloheptyl)-cyclohexanecarboxanilide, and
(e) 3,4-dichloro-N-(2-dimethylaminocycloheptyl)-methoxyacetanilide.

For oral administration, either solid or fluid unit dosage forms of the selected alkanoylanilide can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Wafers are prepared in the same manner as tablets, differing only in shape and the inclusion of sucrose or other sweetener and flavor. In their simplest embodiment, capsules, like tablets, are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum, or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions, the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Rectal suppositories as used herein mean solid bodies for insertion into the rectum which melt or soften at body temperature, releasing one or more pharmacologically or therapeutically active ingredients.

Pharmaceutically acceptable substances utilized in rectal suppositories are bases or vehicles and agents to raise the melting point.

Examples of bases or vehicles include, for example, cocoa butter (theobroma oil), glycerin-gelatin, carbowax, (polyoxyethylene glycol) and appropriate mixtures of mono-, di-, and triglycerides of fatty acids. Combinations of the various bases may be used. Agents to raise the melting point of suppositories include, for example, spermaceti and wax. Rectal suppositories may be prepared either by the compressed method or by molding. The usual weight of a rectal suppository is about 2.0 g.

Tablets and capsules for rectal administration are manufactured utilizing the same pharmaceutically acceptable substance and by the same methods as for formulations for oral administration.

Rectal suppositories, tablets or capsules are packaged either individually, in unit-dose, or in quantity, multiple dose, for example, 2, 6, or 12.

The term unit dosage form, as used in the specification and claims, refers to physically discrete units suitable as unitary dosages for mammals including human subjects, each unit containing a predetermined quantity of active material calculated to produce the desired therapeutic effect in association with the required pharmaceutical diluent, carrier, or vehicle. The specifications for the novel unit dosage forms of this invention are dictated by and directly dependent on (a) the unique characteristics of the active material and the particular effect to be achieved, and (b) the limitations inherent in the art of compounding such an active material for use in humans, as disclosed in detail in this specification, these being features of the present invention. Examples of suitable unit dosage forms in accord with this invention are tablets, capsules, pills, suppositories, powder packets, granules, wafers, cachets, teaspoonfuls, tablespoonfuls, dropperfuls, ampuls, vials, segregated multiples of any of the foregoing, and other forms as herein described.

The dosage of the compound for treatment depends on route of administration, the age, weight and condition of the patient. A dosage schedule of from about 4 to about 400 mg., preferably 50 to 200 mg. per day, given in a single dose or in subdivided doses, embraces the effective range to alleviate depression for which the compositions are effective. The dosage to be administered is calculated on the basis of from about 0.08 to about 6 mg./kg. of weight of the subject. The compound is compounded with a suitable pharmaceutical carrier in unit dosage form for convenient and effective administration. In the preferred embodiments of this invention, the dosage units can contain the compound in 5, 10, 25, 30, 50, 100 and 200 mg. amounts for systemic treatment. A sterile preparation of the active material contains 0.1 percent to 25 percent w/v for parenteral treatment. The dosage of compositions containing a compound of formula I and one or more other active ingredients is to be determined with reference to the actual dosage of each such ingredient.

In addition to the administration of a compound of formula I as the principal active ingredient of compositions for treatment of the conditions desired herein, the said compound can be combined with other compounds such as analgesics, for example, aspirin, acetaminophen, PAC compound (phenacetin-aspirin-caffeine), anti-inflammatory agents such as ibuprofen, and the like, anxiolytics such as perphenazine, amitriptylene hydrochloride, chlordiazepoxide, alprazolam, doxepin hydrochloride, and the like.

EXAMPLE 7

A lot of 10,000 tablets, each containing 40 mg. of trans-3,4-dichloro-N-[2-(dimethylamino)cycloheptyl]-propionanilide maleate salt, as the active ingredient compound, is prepared from the following types and amounts of ingredients:

| | |
|---|---|
| Active ingredient compound | 400 g |
| Dicalcium phosphate | 1,500 g |
| Methylcellulose, U.S.P. (15 cps.) | 60 g |
| Talc | 150 g |
| Corn Starch | 200 g |

| -continued | |
|---|---|
| Magnesium stearate | 12 g |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in reducing depression in adults at a dose of 1 to 2 tablets per day, depending on the age and weight of the patient.

EXAMPLE 8

One thousand two-piece hard gelatin capsules each containing 50 mg. of 3-bromo-N-[2-(dimethylamino)cycloheptyl]propionanilide, hydrochloride salt as the active ingredient compound are prepared from the following types and amounts of ingredients:

| Active ingredient compound | 50 g. |
|---|---|
| Lactose | 75 g. |
| Talc | 25 g. |
| Magnesium stearate | 1.5 g. |

The ingredients are mixed well and filled into capsules of the proper size.

Capsules so prepared are useful for treating depression in adults at a dose of one to two capsules per day.

EXAMPLE 9

One thousand tablets for sublingual use are prepared from the following ingredients:

| 3-trifluoromethyl-N-[2-(dimethylamino)-cycloheptyl]propionanilide, micronized | 10 g. |
|---|---|
| Polyethylene glycol 4,000, powdered | 150 g. |
| Polyethylene glycol 6,000, powdered | 75 g. |

The ingredients are mixed well and compressed into sublingual-type tablets.

These tablets (each containing 10 mg. of active ingredient) placed under the tongue are useful to reduce depression with a rapid reduction at a dose of one tablet per six hours.

EXAMPLE 10

Soft gelatin capsules for oral use, each containing 20 mg. of 3,4-dichloro-N-[2-(diethylamino)cycloheptyl]-propionanilide, methanesulfonate salt, are prepared by first dispersing the micronized compound in corn oil to render the material capsulatable and then encapsulating in the usual manner. These capsules are useful in treatment of depression at a dose of one to two capsules a day.

EXAMPLE 11

One thousand tablets, each containing 60 mg. of 3,4-dichloro-N-[2-(N-pyrrolidinyl)cycloheptyl]propionanilide salt, are made from the following types and amounts of ingredients:

| 3,4-dichloro-[2-(N-pyrrolidinyl)cycloheptyl]propionanilide | 60 g. |
|---|---|
| Lactose | 355 g. |

| -continued | |
|---|---|
| Microocrystalline cellulose NF | 120 g. |
| Starch | 16 g. |
| Magnesium stearate powder | 4 g. |

The ingredients are screened and blended together and pressed into tablets.

The tablets are useful to overcome depression.

EXAMPLE 12

A sterile preparation suitable for intramuscular injection and containing 80 mg. of 3,4-dichloro-N-[2-(dimethylamino)cycloheptyl]propionanilide, hydrochloride salt, in each milliliter is prepared from the following ingredients:

| 3,4-dichloro-N-[2-(dimethylamino)-cycloheptyl]propionanilide, hydrochloride | 80 g. |
|---|---|
| Benzyl benzoate | 200 ml. |
| Methylparaben | 1.5 g. |
| Propylparaben | 0.5 g. |
| Cottonseed oil q.s. | 1,000 ml. |

One milliliter of this sterile preparation is injected to reduce depression in adults.

EXAMPLES 13 TO 25

Following the procedure of the preceding Examples 7 through 12, inclusive, unit dosage forms are similarly prepared substituting equivalent amounts of cis or trans variants of other Formula I compounds; for example
(13) 3-chloro-4-methyl-N-[2-(dimethylamino)cycloheptyl]propionanilide,
(14) 3,4-dichloro-N-{[2-(N-methyl-N-dimethylaminoethyl)amino]cycloheptyl}propionanilide,
(15) 3,4-dimethoxy-N-[2-(dimethylamino)cycloheptyl]-propionanilide,
(16) 3-chloro-4-fluoro-N-[2-(dimethylamino) cycloheptyl]propionanilide,
(17) 3,4-dibromo-N-[2-(dimethylamino)cycloheptyl]-propionanilide,
(18) 3,4-dimethyl-N-[2-(dimethylamino)cycloheptyl]-propionanilide,
(19) 3,4-dichloro-N-[2-(dimethylamino)cycloheptyl]-cyclopropanecarboxanilide,
(20) 3,4-dichloro-N-[2-(dimethylamino)cycloheptyl]-thiopropionanilide,
(21) 3,4-dichloro-N-[2-(N-methyl-N-$\beta$-phenylethylamino)cycloheptyl]propionanilide,
(22) 3,4-dichloro-N-[2-(dimethylamino)cycloheptyl]-propionanilide,
(23) 3-methoxy-N-[2-(dimethylamino)cycloheptyl]propionanilide,
(24) 3,4-dichloro-N-[2-(diethylamino)cycloheptyl]propionanilide,
(25) 3,4-dichloro-N-[2-dimethylaminocycloheptyl]-cyclohexanecarboxanilide, or their pharmacologically acceptable acid addition salts for the respective active ingredients in those examples.

Also, the compounds described hereinbelow (wherein $R_1$ and $R_2$ can be hydrogen, independently or simultaneously) can be substituted into the above-described pharmaceutical formulation examples as the essential active anti-depressant ingredient in chemically-equivalent amounts. For example, the compounds 3,4-dichloro-N-[2-(N-methylamino)cycloheptyl]propionanilide, or 3,4-dichloro-N-(2-aminocycloheptyl)-propionanilide, or a pharmacologically acceptable acid addition salt thereof, can be used.

This invention comprises not only the process for treating depression, the pharmaceutical preparations, including the compounds of Formula I described above, as the essential active anti-depressant ingredients, but also includes such process for treating depression using the new pharmaceutical preparations containing compounds of Formula I above wherein p, Q, R, Y and Z are as defined above; and, $R_1$ and $R_2$ are each hydrogen or one of $R_1$ and $R_2$ is hydrogen and the other of $R_1$ and $R_2$ is $C_1$ to $C_3$-alkyl as well as the pharmaceutical preparations per se, and some compounds per se. These latter compounds are described here because they are prepared by a synthesis procedure that is somewhat different from that described above where each of $R_1$ and $R_2$ is some group other than hydrogen.

The trans compounds wherein $R_1$ and $R_2$ are both hydrogen or when one of $R_1$ and $R_2$ is hydrogen, the other of $R_1$ and $R_2$ is alkyl as defined above, and p, Q, R, Y and Z are as defined above, are prepared in the manner described below:

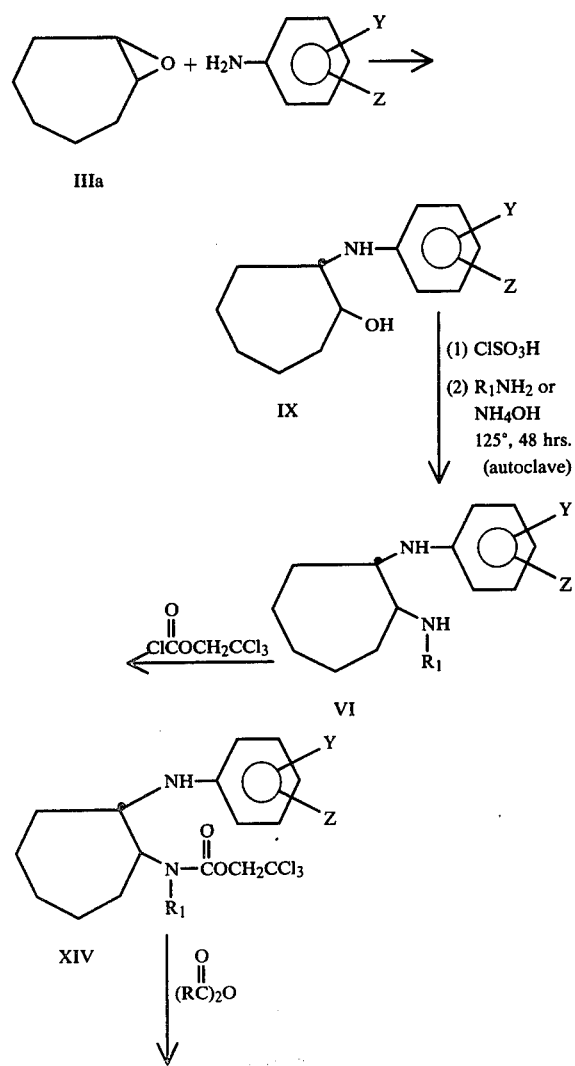

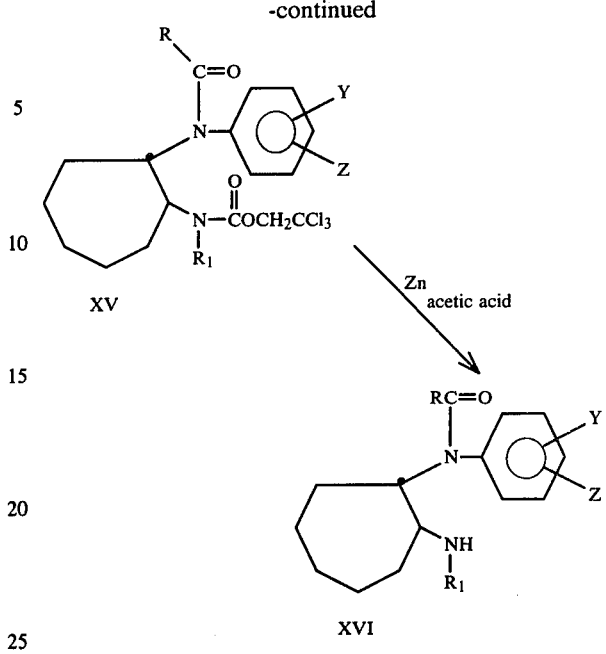

Reaction of the cycloheptene oxide IIIa with an aniline under conditions well known in the art gives the N-(2-hydroxycycloheptyl)-aniline IX which, when reacted with chlorosulfonic acid in a non-polar organic solvent, e.g., methylene chloride, at 20°–30° C., followed by heating with a selected $C_1$ to $C_3$-monoalkylamine (aqueous) or ammonium hydroxide (aqueous) at 100°–150° C. for 40–55 hours at elevated pressure (2–10 atm.), gives the diamine VI. Reaction of diamine VI with 2,2,2-trichloroethyl chloroformate, or equivalent N-blocking compound, at 20°–30° C. for 1–5 hours proceeds in the presence of an acid scavenger, e.g., triethylamine, to give the 2-(N-blocked amino) compound XIV. Acylation of the N-blocked compound XIV with the selected acid anhydride,

by heating at 90°–120° C. for 12 to 30 hours gives the N-blocked anilide XV. Deprotection of the 2-amino function of the 2-N-blocked anilide XV is then accomplished by reaction with an N-deblocking agent such as metal dust in acid, e.g., zinc in acetic acid, in a polar organic solvent, e.g., methanol, at 20°–100° C. for 2 to 6 hours. Work-up, isolation and purification procedures are those standard in the art of organic chemistry.

Preparation of the cis isomeric compound XVII is carried out as described previously

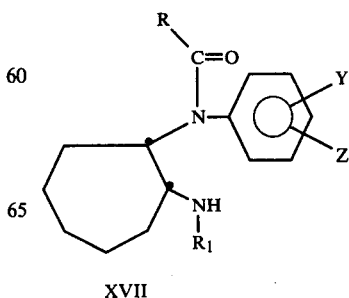

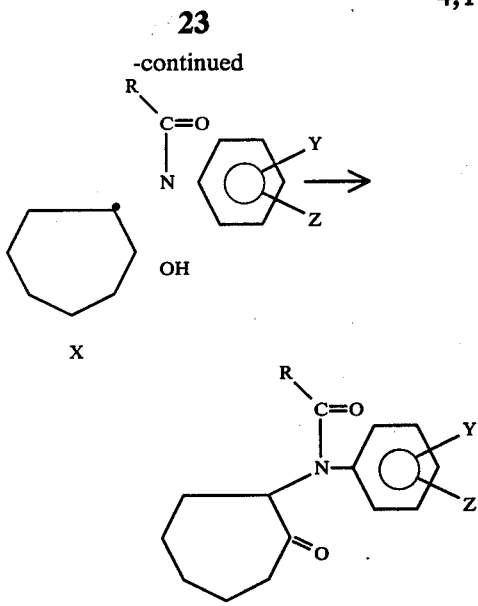

X in this specification by oxidation of the 2-hydroxycycloheptylanilide X with a known oxidizing agent, e.g., Jones Reagent, to the ketone XI, which, when reacted with a $C_1$ to $C_3$-monoalkyl amine or ammonium acetate in the presence of a reducing agent, e.g., sodium cyanoborohydride, gives mixed isomer amino anilide XVIII.

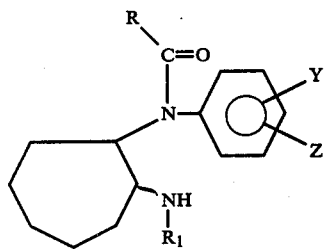

Chromatographic separation of the two isomers can be effected to give the cis amino anilide XVII, wherein $R_1$ is hydrogen or $C_1$ to $C_3$-alkyl.

A preferred group of the above genus compounds which includes those compounds wherein one or both of $R_1$ and $R_2$ are hydrogen and the pharmaceutical preparation forms thereof are those wherein R is $C_1$ to $C_3$-alkyl, preferably ethyl, $R_1$ and $R_2$ are each hydrogen or one of $R_1$ and $R_2$ is hydrogen and the other of $R_1$ and $R_2$ is $C_1$ to $C_3$-alkyl, preferably methyl, and at least one of Y and Z is halogen having an atomic number of from 9 to 35, preferably in the 3- and 4-positions, trifluoromethyl in the 3-position, or methyl in the 3- or 4-position in combination with one of the above halogens at the adjacent 3- or 4-position, and the pharmacologically acceptable salts thereof. Examples of such compounds include the following:

3,4-dichloro-N-[2-(N-methylamino)cycloheptyl]propionanilide;
3-trifluoromethyl-N-[2-(N-methylamino)cycloheptyl]propionanilide;
3,4-dichloro-N-[2-(N-ethylamino)cycloheptyl]propionailide;
3-chloro-4-methyl-N-[2-aminocycloheptyl]propionanilide;
4-chloro-3-methyl-N-[2-(N-methylamino)cycloheptyl]propionailide;
3-chloro-N-[2-(N-methylamino)cycloheptyl]propionanilide;
4-chloro-N-[2-aminocycloheptyl]propionanilide;
3-bromo-N-[2-aminocycloheptyl]propionanilide; and
3-fluoro-N-[2-(N-methylamino)cycloheptyl]propionanilide; especially these compounds in the transconfigurations, and the pharmacologically acceptable salts thereof.

This latter preferred group of compounds having an unsubstituted amino or a mono-$C_1$ to $C_3$-alkyl-substituted amino group in the 2-position of the cycloheptyl ring have anti-depressant properties in standard laboratory animal tests such as the standard yohimbine toxicity potentiation and oxotremorine hypothermia antagonism tests, indicating quite potent anti-depressant properties of these compounds so that the 2-amino- and 2-(N-methylamino)cycloheptyl anilides have similar properties and uses as the above-described N-[2-(N,N-disubstituted-amino)-cycloheptyl]anilide compounds in about the same dosage ranges as indicated above.

EXAMPLE 26

Trans-3,4-dichloro-N-[2-(N-methylamino)cycloheptyl]-propionanilide and its p-toluenesulfonate salt. Method A.

Trans-N-(2-hydroxycycloheptyl)-3,4-dichloroaniline and its hydrochloride salt

A solution of 3,4-dichloroaniline, cycloheptene oxide, and concentrated HCl (2 ml.) is heated at reflux temperature for seven (7) days. The unreacted epoxide is evaporated and the residue is treated with excess ethereal HCl, and a syrup results. This is washed with ether. The residue is crystallized and recrystallized from methanol/ether (1/5.5, v/v) to give trans-3,4-dichloro-N-(2-hydroxycycloheptyl)aniline, hydrochloride salt.

B.
Trans-3,4-dichloro-N-(2-sulfonyloxycycloheptyl)aniline

To a stirred solution/suspension of amino-alcohol salt from Part A, trans-3,4-dichloro-N-(2-hydroxycycloheptyl)aniline hydrochloride, in methylene chloride, there is added an equimolar amount of chlorosulfonic acid in methylene chloride over a 4-hour period. Complete solution of the amino alcohol is effected when addition of the acid solution is about one-half completed. The mixture is stirred overnight. The precipitate which forms is collected, washed with methylene chloride and ethyl ether and dried in an oven at 45° C. The subtitled product is obtained.

C.
Trans-3,4-dichloro-N-[2-(N-methylamino)cycloheptyl]-aniline and its dihydrochloride salt A portion of 3,4-dichloro-N-(2-sulfonyloxycycloheptyl)-aniline is reacted with an equimolar amount of 40% mono-methylamine in water at 125° C. for 48 hours (in autoclave) to form trans-3,4-dichloro-N-[2-(N-methylamino)cycloheptyl]aniline in solution.

The reaction product mixture is washed with a 1:1 v/v water/ethyl ether mixture. The organic layer is removed from the aqueous layer and the aqueous layer is extracted with ethyl ether. The combined ether layers are washed with saturated sodium chloride solution, dried over magnesium sulfate, and evaporated to an oil.

This oil is chromatographed on silica gel, eluting with ethyl acetate and methanol. The late fractions contain the diamine product, trans-3,4-dichloro-N-[2-(N-methylamino)cycloheptyl]aniline. The forerun is a mixture. The forerun is rechromatographed on silica gel, again eluting with ethyl acetate and methanol, collecting the eluate in 500 ml. fractions. Again, the first fractions of this second chromatography are a forerun; the latter fractions contain more of the amine product. After evaporation of solvent, the diamine fractions give an oil. This diamine product oil is converted to its hydrochloride salt with excess ethyl ether/hydrochlogen chloride solution. The sub-titled diamine hydrochloride salt is recrystallized from methanol and ethyl ether.

A further run of this reaction starting from the amino alcohol and without recovering the intermediate 2-sulfonyloxy compound is run as follows:

To a stirred solution of the amino-alcohol salt, trans-3,4-dichloro-N-(2-hydroxycycloheptyl)aniline hydrochloride, in chloroform, there is added chlorosulfonic acid in chloroform over 15 minutes. The mixture is placed in a warm water bath to accelerate evolution of hydrogen chloride by-product. The resulting reaction mixture solution is concentrated and the residue dissolved in 40% monomethylamine in water. The resulting mixture is heated overnight in a bomb reactor at 125° C. The resulting reaction mixture is cooled and extracted with ethyl ether. The ether extract is washed with saturated sodium chloride and dried over magnesium sulfate and then evaporated to a yellow oil. The oil is chromatographed on silica gel, eluting with ethyl acetate to remove amino-alcohol starting material. The oil in the chromatography column is then eluted with methanol and gives crude oil product after evaporation of solvent. This sub-titled diamine oil product, trans-3,4-dichloro-N-[2-(N-methylamino)cycloheptyl]aniline, is converted to its hydrochloride salt with excess ethyl ether-hydrochlogen chloride solution and is then recrystallized from methanol in ethyl ether.

D.
Trans-3,4-dichloro-N-[2-(N-methyl-N-trichloroethoxycarbonylamino)cycloheptyl]aniline hydrochloride To a mixture of equimolar quantities of triethylamine and the free diamine, trans-3,4-dichloro-N-[2-(N-methylamino)cycloheptyl]-aniline, released from its hydrochloride salt with sodium hydroxide, in ethyl ether, there is added an equimolar amount of 2,2,2-trichloroethyl chloroformate in ethyl ether. The mixture is stirred at room temperature for 2 hours. Then saturated sodium bicarbonate solution is added. The organic layer is dried over magnesium sulfate and concentrated to an oil. This oil is converted to its hydrochloride salt by treatment with excess ethereal hydrochloric acid. This sub-titled salt is recrystallized from a mixture of methanol and ethyl ether.

E.
Trans-3,4-dichloro-N-[2-(N-methyl-N-trichloroethoxycarbonylamino)cycloheptyl]propionanilide A mixture of the diamine, prepared as in part D above and converted to its free base, and propionic acid anhydride is heated on a steam bath overnight. Then water is added and the mixture heated for 1 hour. The mixture is diluted with ethyl ether. The organic layer is washed with 15% sodium hydroxide solution and with saturated sodium chloride, dried over magnesium sulfate, and evaporated to an oil, the subtitled propionanilide.

In another run, going through 2 steps without isolation of the 2-N-blocked diamine (Part D) 2,2,2-trichloroethyl chloroformate in ethyl ether is added over one-half hour with ice cooling to a mixture of equimolar amounts of triethylamine and the diamine, trans-3,4-dichloro-N-[2-(N-methylamino)cycloheptyl]aniline, released from its hydrochloride salt, in ethyl ether. After stirring at room temperature for 2 hours, saturated sodium bicarbonate aqueous solution is added. The organic layer is washed with saturated sodium chloride solution, dried over magnesium sulfate and evaporated to an oil. Then propionic acid anhydride is added to the oil and the solution is heated overnight on a steam bath. Then water is added and the mixture is heated with stirring for one hour. The mixture is made basic with 15% sodium hydroxide and extracted with ethyl ether. The ethyl ether extract is washed with saturated sodium chloride, dried over magnesium sulfate, and evaporated to an oil product, the subtitled propionanilide.

F.
Trans 3,4-dichloro-N-[2-(N-methylamino)cycloheptyl]-propionanilide and its p-toluenesulfonate salt The N-blocked propionanilide, from E above, and a large excess of zinc dust in 5% acetic acid in methanol is stirred at room temperature for 3 hours, refluxed for 1 hour, and cooled to room temperature. The mixture is then filtered through a filter aid (Celite ®) and washed with methanol. The solvent is evaporated and the residue treated with 5 N ammonium hydroxide and ethyl ether. The ether extract is washed with saturated sodium chloride solution, dried over magnesium sulfate and evaporated to an oil (the subtitled propionanilide). This propionanilide is converted to its p-toluenesulfonate salt by treating the oil with p-toluenesulfonic acid in methanol and ethyl ether.

EXAMPLE 27
Trans-3,4-dichloro-N-[2-(N-methylamino)cycloheptyl]-propionanilide, and its p-toluenesulfonate salt - Method B A mixture of 3,4-dichloro-N-[2-(dimethylamino)cycloheptyl]propionanilide, released from its maleate salt (Example 1) with sodium hydroxide, and an excess of mercuric acetate in 5% acetic acid in water is heated on a steam bath. The precipitate which results is filtered and washed with 10% hydrochloric acid solution. A small amount of precipitate is removed by filtration. The solution (filtrate) is made basic with concentrated ammonium hydroxide and extracted with ethyl ether. The ether extract is washed with saturated sodium chloride solution, dried over magnesium sulfate and evaporated to an oil. This oil is converted to its p-toluenesulfonate salt with p-toluenesulfonate acid in a methanol ethyl ether solution. After recrystallization there is obtained the titled propionanilide salt.

EXAMPLE 28
Trans-3,4-dichloro-N-(2-aminocycloheptyl)-propionanilide and its β-naphthylsulfonate salt A. Trans-3,4-dichloro-N-(2-aminocycloheptyl)aniline and its hydrochloride A mixture of 3,4-dichloro-N-(2-sulfonyloxycycloheptyl)aniline (from Example 26, Part B) and an excess of 17 N ammonium hydroxide is heated in a sealed bottle at 125° C. for 48 hours. The mixture is then cooled to room temperature. The contents of the bottle are dissolved in a mixture of ethyl ether and water. The ether layer is washed with saturated sodium chloride solution, dried over magnesium sulfate and concentrated to an oil. This oil is chromatographed on silica gel eluting with ethyl acetate followed by methanol. A thin layer chromatographic (TLC) analysis of the last methanol fraction shows that it contains the subtitled diamine product. After evaporating the bulk of the methanol from the amine, the residue is treated with excess ethyl ether-hydrogen chloride solution to form the diamine hydrochloride salt. The salt is recrystallized from a mixture of methanol and ethyl ether to obtain the subtitled diamine hydrochloride salt.

B.
Trans-3,4-dichloro-N-[2-(N-trichloroethoxycarbonylamino)cycloheptyl]aniline, and the hydrochloride salt.

To a mixture of diamine from Part A above, released from its hydrochloride salt, and an equimolar amount of triethylamine, in ethyl ether, cooled in ice, there is added an equimolar amount of 2,2,2-trichloroethyl chloroformate in ethyl ether. The resulting mixture is stirred over the weekend at room temperature. Then saturated aqueous sodium bicarbonate solution is added. The organic layer is washed with saturated sodium chloride solution, dried over magnesium sulfate, and concentrated to an oil residue, the subtitled aniline. The hydrochloride salt is prepared by treating the oil residue with excess ether-hydrogen chloride solution. The salt is recrystallized from a mixture of methanol and ethyl ether to obtain the subtitled aniline salt. The filtrate is evaporated and the residue is recrystallized from a mixture of methanol and ethyl ether to obtain additional aniline salt.

C.
Trans-3,4-dichloro-N-[2-(2,2,2-trichloroethoxycarbonylamino)cycloheptyl]propionanilide A mixture of trans-3,4-dichloro-N-[2-(2,2,2-trichloroethoxycarbonylamino)cycloheptyl]aniline and propionic acid anhydride is heated on a steam bath overnight. Then water is added and the mixture is heated for 1 hour. The mixture is diluted with ethyl ether. The organic layer which develops is separated from the aqueous layer and washed with 15% sodium hydroxide and with saturated sodium chloride solution, dried over magnesium sulfate and evaporated to a solid which is triturated with ethyl ether and petroleum ether. There is obtained the subtitled N-blocked propionanilide compound.

D.
Trans-3,4-dichloro-N-(2-aminocycloheptyl)propionanilide, and its β-naphthylsulfonate salt A mixture of trans-3,4-dichloro-N-[2-(2,2,2-trichloroethoxycarbonylamino)cycloheptyl]propionanilide from Part C above, and a large molar excess of zinc dust in 5% acetic acid in methanol solution is stirred at room temperature overnight. The mixture is filtered through a filter aid (Celite ®) and washed with methanol. The filtrate is evaporated and the residue is treated with 5 N ammonium hydroxide and ethyl ether. The ethyl layer is washed with saturated sodium chloride solution, dried over magnesium sulfate and concentrated to an oil, the subtitled propionanilide, which is converted to its napsylate (β-naphthylsulfonate) salt in a methanol-ethyl ether solution using an equimolar amount of β-naphthylsulfonic acid.

I claim:
1. A process for treating depression which comprises administering to a depressed human a compound of the formula

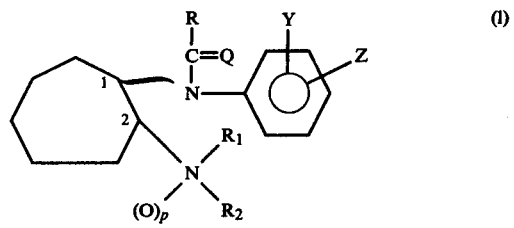

wherein the wavy line (∼) in the 1-position of the cycloheptyl ring indicates cis or trans configuration of the substituents in the 1- and 2-positions of the cycloheptyl ring;
p is zero or 1;
Q is oxygen or sulfur;
R is $C_1$ to $C_3$-alkyl;
$R_1$ and $R_2$ are taken together with the nitrogen to which they are bonded to complete an N-pyrrolidinyl or N-piperidinyl ring;
each of Y and Z is selected from the group consisting of hydrogen, a halogen having an atomic number of from 9 to 35, trifluoromethyl, $C_1$ to $C_2$-alkyl, and $C_1$ to $C_2$-alkyloxy and when Y is trifluoromethyl, Z is hydrogen; when Y is $C_1$ to $C_2$-alkyloxy and Z is hydrogen, the $C_1$ to $C_2$-alkyloxy is in the 3-position; when Y and Z are both halogens or $C_1$ to $C_2$-alkyloxy, they are present in the 3- and 4- or 3- and 5-positions, or a pharmacologically acceptable salt thereof, in an amount effective to alleviate the conditions of depression, in association with a pharmaceutical carrier.

2. A process in accordance with claim 1 wherein the compound of Formula I is administered in unit dosage form ranging from 4 to 400 mg. of the Formula I compound or its pharmacologically acceptable acid addition salt.

3. A process according to claim 1 wherein the Formula I compound is one in which R is $C_1$ to $C_3$-alkyl, $R_1$ and $R_2$ are taken together with the nitrogen to which they are bonded to complete an N-pyrrolidinyl or N-piperidinyl moiety, and at least one of Y and Z is a halogen having an atomic number of from 9 to 35, in the 3- or 4-position, or a pharmacologically acceptable salt thereof.

4. A process according to claim 3 wherein the compound is 3,4-dichloro-N-[2-(N-pyrrolidinyl)cycloheptyl]propionanilide, or a pharmacologically acceptable salt thereof.

5. A pharmaceutical preparation in dosage unit form adapted for administration to obtain an anti-depression effect comprising per dosage unit, an anti-depressant effective, non-toxic amount ranging from 4 to 400 mg. per dosage unit of a compound of the formula

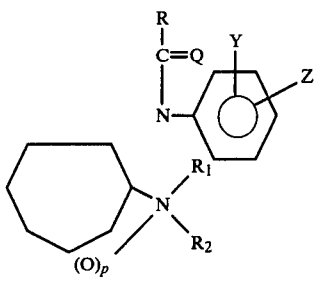

(I)

wherein the wavy line (∼) in the 1-position of the cycloheptyl ring indicates cis or trans configuration of the substituents in the 1- and 2- positions of the cycloheptyl ring;
 p is zero or 1;
 Q is oxygen or sulfur;
 R is $C_1$ to $C_3$-alkyl,
 $R_1$ and $R_2$ are taken together with the nitrogen to which they are bonded to complete an N-pyrrolidinyl or N-piperidinyl ring;
 each of Y and Z is selected from the group consisting of hydrogen, a halogen having an atomic number of from 9 to 35, trifluoromethyl, $C_1$ to $C_2$-alkyl, and $C_1$ to $C_2$-alkyloxy and when Y is trifluoromethyl, Z is hydrogen; when Y is $C_1$ to $C_2$-alkyloxy and Z is hydrogen, the $C_1$ to $C_2$-alkyloxy is in the 3-position; when Y and Z are both halogens or $C_1$ to $C_2$-alkyloxy, they are present in the 3- and 4- or 3- and 5- positions, or a pharmacologically acceptable salt thereof, and a pharmaceutical diluent.

6. A pharamceutical preparation according to claim 5 wherein the compound of Formula I is in the trans configuration.

7. A pharmaceutical preparation according to claim 5 wherein the compound of Formula I is in the cis configuration.

8. A pharmaceutical preparation according to claim 5 wherein in the Formula I compound R is $C_1$ to $C_3$-alkyl, $R_1$ and $R_2$ are taken together with the nitrogen to which they are bonded to complete an N-pyrrolidinyl or N-piperidinyl moiety, and at least one of Y and Z is a halogen having an atomic number of from 9 to 35, in the 3- or 4-position, or a pharmacologically acceptable salt thereof.

9. A pharmaceutical preparation according to claim 8 wherein the Formula I compound is 3,4-dichloro-N-[2-(N-pyrrolidinyl)cycloheptyl]propionanilide, or a pharmacologically acceptable salt thereof.

10. 3,4-Dichloro-N-[2-(N-pyrrolidinyl)cycloheptyl]-propionanilide, and the pharmacologically acceptable salts thereof.

* * * * *

UNITED STATES PATENT AND TRADEMARK OFFICE
CERTIFICATE OF CORRECTION

PATENT NO. : 4,159,339

DATED : June 26, 1979

INVENTOR(S) : Jacob Szmuszkovicz

It is certified that error appears in the above-identified patent and that said Letters Patent are hereby corrected as shown below:

Front Page [54] "N-(2-AMINOCYCLOHEPTYL)ALKANOYLANILIDES" should read --N-(2-AMINOCYCLOHEPTYL)ALKANOYLANILIDES AND IN THE TREATMENT OF DEPRESSION--.

[60] "March 15, 1978" should read --March 13, 1978--.

Column 1, line 1: "N-(2-AMINOCYCLOHEPTYL)ALKANOYLANILIDES" should read --N-(2-AMINOCYCLOHEPTYL)ALKANOYLANILIDES AND IN THE TREATMENT OF DEPRESSION--.

Column 2, line 49: "P" should read --p--.
Column 2, line 52: "examples" should read --example--.
Column 4, line 31: "3chloro" should read --3-chloro--.
Column 11, line 9: "benzylamino9cyclo" should read --benzylamino)cyclo--.
Column 13, line 16: "heptane-1-ol.." should read --heptan-1-ol--.

Column 15, line 41: "3A" should read --3$\overset{O}{A}$--.

Column 23, Drawing 10, approx. line 5:

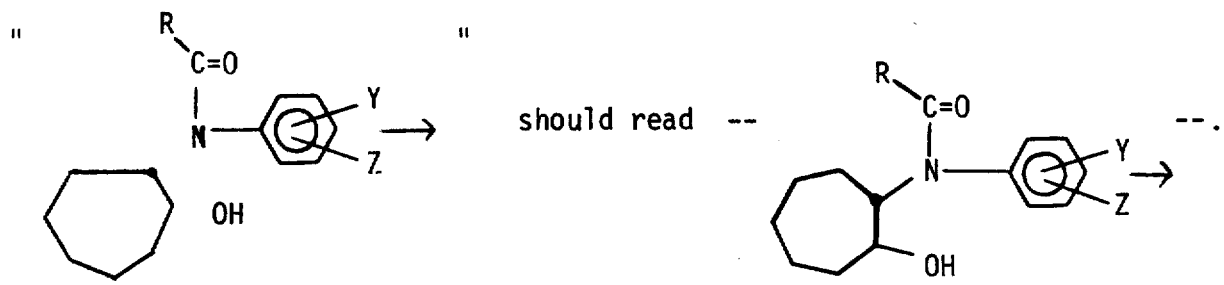

UNITED STATES PATENT AND TRADEMARK OFFICE
CERTIFICATE OF CORRECTION

PATENT NO. : 4,159,339

DATED : June 26, 1979

INVENTOR(S) : Jacob Szmuszkovicz

It is certified that error appears in the above-identified patent and that said Letters Patent are hereby corrected as shown below:

Column 29, Drawing I, approx. line 5:

" 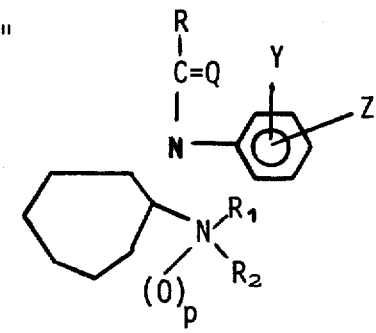 " should read -- 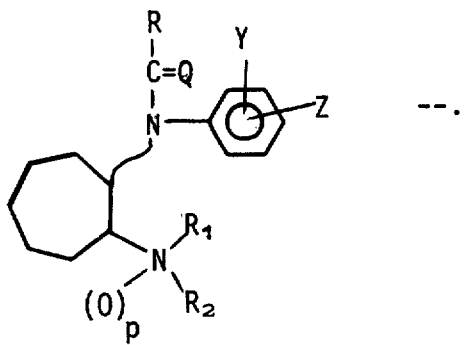 --.

Signed and Sealed this

Eleventh Day of December 1979

[SEAL]

Attest:

SIDNEY A. DIAMOND

Attesting Officer     Commissioner of Patents and Trademarks